(12) United States Patent
Dickman et al.

(10) Patent No.: US 9,173,620 B2
(45) Date of Patent: Nov. 3, 2015

(54) IMAGING SYSTEM WITH RIGIDLY MOUNTED FIDUCIAL MARKERS

(71) Applicant: NeuroLogica Corp., Danvers, MA (US)

(72) Inventors: Matthew Dickman, Chelsea, MA (US); Eric Bailey, Hampton, NH (US); Andrew Tybinkowski, Boxford, MA (US); Michael Limoli, Merrimac, MA (US)

(73) Assignee: NeuroLogica Corp., Danvers, MA (US)

( * ) Notice: Subject to any disclaimer, the term of this patent is extended or adjusted under 35 U.S.C. 154(b) by 121 days.

(21) Appl. No.: 13/863,968

(22) Filed: Apr. 16, 2013

(65) Prior Publication Data

US 2013/0272489 A1  Oct. 17, 2013

Related U.S. Application Data

(60) Provisional application No. 61/624,522, filed on Apr. 16, 2012, provisional application No. 61/624,537, filed on Apr. 16, 2012.

(51) Int. Cl.
*A61B 6/03* (2006.01)
*A61B 6/00* (2006.01)
*A61B 19/00* (2006.01)

(52) U.S. Cl.
CPC ............ *A61B 6/035* (2013.01); *A61B 6/032* (2013.01); *A61B 6/4405* (2013.01); *A61B 6/548* (2013.01); *A61B 6/56* (2013.01); *A61B 19/2203* (2013.01); *A61B 2019/505* (2013.01); *A61B 2019/524* (2013.01); *A61B 2019/5251* (2013.01); *A61B 2019/5255* (2013.01); *A61B 2019/5289* (2013.01); *A61B 2019/5483* (2013.01)

(58) Field of Classification Search
CPC .......... A61B 6/035; A61B 6/58; A61B 6/582; A61B 6/583; A61B 6/584; A61B 6/032; G01N 23/046
USPC .......................... 378/15, 18, 207, 4, 196–200
See application file for complete search history.

(56) References Cited

U.S. PATENT DOCUMENTS

| | | | |
|---|---|---|---|
| 3,603,975 A | 9/1971 | Gordon | |
| 4,341,220 A | 7/1982 | Perry | |
| 5,075,554 A | 12/1991 | Yunker et al. | |
| 5,425,069 A | 6/1995 | Pellegrino et al. | |
| 5,499,284 A | 3/1996 | Pellegrino et al. | |
| 5,703,921 A * | 12/1997 | Fujita et al. | 378/4 |
| 5,887,047 A | 3/1999 | Bailey et al. | |
| 5,982,843 A | 11/1999 | Bailey et al. | |
| 6,108,396 A | 8/2000 | Bechwati et al. | |
| 6,199,233 B1 | 3/2001 | Kantrowitz et al. | |
| 6,256,404 B1 | 7/2001 | Gordon et al. | |
| 6,285,028 B1 | 9/2001 | Yamakawa | |
| 6,314,157 B1 * | 11/2001 | Tachizaki | 378/4 |
| 6,337,894 B1 | 1/2002 | Tybinkowski et al. | |
| 6,374,937 B1 | 4/2002 | Galando et al. | |
| 6,396,902 B2 | 5/2002 | Tybinkowski et al. | |
| 6,519,312 B1 * | 2/2003 | Tybinkowski et al. | 378/4 |
| 6,590,953 B2 * | 7/2003 | Suzuki et al. | 378/15 |
| 6,733,177 B2 * | 5/2004 | Pillai et al. | 378/198 |

(Continued)

*Primary Examiner* — Allen C. Ho
(74) *Attorney, Agent, or Firm* — Pandiscio & Pandiscio

(57) ABSTRACT

An imaging system including a scanner having scanning components for creating an image of an interior portion of an object; an outer cover disposed over the scanning components; an opening formed in the outer cover; and a rigid mount which is rigidly mounted to the scanning components and extends through the opening formed in the outer cover.

26 Claims, 13 Drawing Sheets

(56) References Cited

U.S. PATENT DOCUMENTS

| | | | | |
|---|---|---|---|---|
| 6,789,941 | B1 * | 9/2004 | Grady | 378/197 |
| 6,813,374 | B1 | 11/2004 | Karimi et al. | |
| 6,857,778 | B2 | 2/2005 | Mun et al. | |
| 6,890,100 | B2 * | 5/2005 | Reznicek et al. | 378/207 |
| 6,909,775 | B2 * | 6/2005 | Ray et al. | 378/141 |
| 6,914,957 | B2 * | 7/2005 | Dafni et al. | 378/15 |
| 6,940,941 | B2 * | 9/2005 | Gregerson et al. | 378/4 |
| 7,010,081 | B2 * | 3/2006 | Brunnett et al. | 378/15 |
| 7,016,467 | B2 | 3/2006 | Brooks | |
| 7,020,233 | B1 * | 3/2006 | Tybinkowski et al. | 378/4 |
| 7,072,434 | B1 * | 7/2006 | Tybinkowski et al. | 378/4 |
| 7,108,421 | B2 * | 9/2006 | Gregerson et al. | 378/197 |
| 7,175,347 | B2 * | 2/2007 | Tybinkowski et al. | 378/198 |
| 7,374,337 | B2 * | 5/2008 | Yunker | 378/198 |
| 7,374,338 | B2 * | 5/2008 | Distler et al. | 378/199 |
| 7,384,194 | B2 * | 6/2008 | Gatten | 378/208 |
| 7,396,160 | B2 * | 7/2008 | Tybinkowski et al. | 378/199 |
| 7,397,895 | B2 * | 7/2008 | Bailey et al. | 378/102 |
| 7,438,471 | B2 * | 10/2008 | Tybinkowski et al. | 378/198 |
| 7,447,294 | B2 * | 11/2008 | Sadotomo et al. | 378/4 |
| 7,486,775 | B2 * | 2/2009 | Forster et al. | 378/137 |
| 7,514,885 | B2 * | 4/2009 | Hausner et al. | 318/268 |
| 7,568,836 | B2 * | 8/2009 | Bailey et al. | 378/198 |
| 7,637,660 | B2 * | 12/2009 | Tybinkowski et al. | 378/198 |
| 7,751,865 | B2 * | 7/2010 | Jascob et al. | 600/424 |
| 7,806,590 | B2 * | 10/2010 | Jimbo et al. | 378/199 |
| 7,885,376 | B2 * | 2/2011 | Sasaki et al. | 378/15 |
| 7,889,837 | B2 * | 2/2011 | Takamatsu et al. | 378/19 |
| 7,938,579 | B2 * | 5/2011 | Groβ et al. | 378/197 |
| 8,023,615 | B2 * | 9/2011 | Fukushima et al. | 378/4 |
| 8,057,097 | B1 * | 11/2011 | Tybinkowski et al. | 378/203 |
| 8,237,123 | B2 * | 8/2012 | Yakubovsky et al. | 250/363.02 |
| 8,320,659 | B2 * | 11/2012 | Song et al. | 382/143 |
| 8,596,865 | B2 * | 12/2013 | Nyholm et al. | 378/196 |
| 8,657,809 | B2 * | 2/2014 | Schoepp | 606/1 |
| 8,681,931 | B2 * | 3/2014 | Hyvarinen et al. | 378/4 |
| 8,684,599 | B2 * | 4/2014 | Seppala et al. | 378/197 |
| 8,686,368 | B2 * | 4/2014 | Tybinkowski et al. | 250/363.05 |
| 8,721,177 | B2 * | 5/2014 | Jimbo et al. | 378/199 |
| 8,746,974 | B2 * | 6/2014 | Seppala et al. | 378/197 |
| 8,753,009 | B2 * | 6/2014 | Gregerson et al. | 378/196 |
| 8,903,038 | B2 * | 12/2014 | Matsuzawa et al. | 378/13 |
| 8,912,499 | B2 * | 12/2014 | Asagiri et al. | 250/370.11 |
| 8,971,482 | B2 * | 3/2015 | Bailey et al. | 378/20 |
| 8,998,797 | B2 * | 4/2015 | Omori | 600/102 |
| 9,001,964 | B2 * | 4/2015 | Neushul et al. | 378/19 |
| 9,044,152 | B2 * | 6/2015 | Abenaim et al. | 1/1 |
| 2003/0185338 | A1 | 10/2003 | Dafni et al. | |
| 2004/0122311 | A1 | 6/2004 | Cosman | |
| 2004/0146142 | A1 | 7/2004 | Maijala | |
| 2005/0085714 | A1 | 4/2005 | Foley et al. | |
| 2005/0085720 | A1 | 4/2005 | Jascob et al. | |
| 2007/0183588 | A1 | 8/2007 | Bailey et al. | |
| 2008/0008290 | A1 | 1/2008 | Tybinkowski et al. | |
| 2008/0221520 | A1 | 9/2008 | Nagel et al. | |
| 2009/0005677 | A1 | 1/2009 | Weber et al. | |
| 2009/0034790 | A1 | 2/2009 | Song et al. | |
| 2009/0192519 | A1 | 7/2009 | Omori | |
| 2012/0078236 | A1 | 3/2012 | Schoepp | |
| 2013/0272488 | A1 * | 10/2013 | Bailey et al. | 378/4 |

* cited by examiner

IMAGING SYSTEM WITH RIGIDLY MOUNTED FIDUCIAL MARKERS

The two (2) above-identified patent applications are hereby incorporated herein by reference.

FIELD OF THE INVENTION

This invention relates to anatomical imaging systems in general, and more particularly to imaging systems used in conjunction with surgical guidance systems.

BACKGROUND OF THE INVENTION

Strokes are currently the third leading cause of death in the United States, causing approximately 177,000 deaths per year, and strokes are currently the number one cause of long-term disability in the United States, currently affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate blood clots, is contra-indicated for a hemorrhagic stroke. Furthermore, the clinical data suggests that the medication used to treat ischemic strokes (i.e., tPA) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hour window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke).

Computerized Tomography (CT) has emerged as the key imaging modality in the diagnosis of strokes. CT scanners generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning, including non-enhanced CT scanning, CT angiography scanning and CT perfusion scanning, is able to provide substantially all of the information needed to effectively diagnose (and hence properly treat) a stroke.

Unfortunately, in practice, the CT machine is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient (e.g., it can prevent ischemic stroke victims from being timely treated with tPA).

Thus, there is an urgent need for a new and improved CT machine which is particularly well suited for use in stroke applications. More particularly, there is an urgent need for a small, mobile CT machine which can be pre-positioned in the emergency room and moved to the patient so that the patient can be scanned at their current location, thus effectively eliminating "round-trip" delays and dramatically reducing the time needed to properly diagnose the patient. It is also important that the CT machine be relatively inexpensive, so as to facilitate its rapid proliferation and widespread use, e.g., pre-positioning in substantially all hospital emergency rooms and wide availability in outlying, low-volume settings (e.g., rural hospitals, ships, etc.).

In this respect it should also be appreciated that current CT scanners are typically accompanied by a significant amount of physical cabling. This physical cabling generally takes the form of (i) electrical cables used to deliver electrical power to the CT scanner, and (ii) networking cables used to connect the CT scanner to a workstation, whereby to permit medical personnel to issue scanning instructions to the CT scanner using the workstation, and whereby to enable the CT scanner to send images and scanner data to the workstation for viewing by medical personnel. The workstation can, in turn, be connected to a hospital PACs (Picture Archive and Communication) system or other IT network, so as to permit the CT scanner to be controlled from remote locations and so as to permit images and scanner data to be viewed by medical personnel at remote locations. Alternatively, the CT scanner can be directly connected to a hospital PACs system or other IT network.

The aforementioned physical cabling generally does not present significant issues with conventional CT scanners, since such conventional CT scanners are designed for fixed-position installations. Thus, with fixed-position CT scanners, the disposition of the physical cabling can be addressed at the time of CT scanner installation so as to make the physical cabling relatively inobtrusive (e.g., the physical cabling can be carefully positioned so that it is out of the way of patients and medical personnel).

However, if the CT scanner is to be highly mobile so that the CT scanner can be brought to the bedside of the patient, conventional physical cabling presents a significant problem, since it can interfere with the delivery of time-critical medical treatment and present a physical hazard to medical personnel focused on delivering such medical treatment.

By way of example but not limitation, suppose a patient arrives in an emergency room presenting symptoms of stroke. In this situation, it is imperative that CT scanning be effected as quickly as possible, even as other medical testing and/or treatment is being administered to the patient. Medical personnel must work quickly and efficiently in this situation, with their focus on the delivery of time-critical patient care. If a mobile CT scanner were equipped with conventional physical cabling, bringing the mobile CT scanner to the patient would require the introduction of this conventional physical cabling to the point of care. This physical cabling would present a significant intrusion into the point of care, complicating the delivery of time-critical medical treatment and presenting a physical hazard to medical personnel working around the patient. This is particularly true where the mobile CT scanner is deployed hurriedly, e.g, in the case of a possible stroke patient just arriving at an emergency room.

Thus, there is a need for a new and improved approach for (i) providing the electrical power needed to operate the mobile CT scanner, and (ii) connecting the CT scanner to a workstation, hospital PACs system or other IT network, all without the use of the physical cabling normally associated with a conventional CT scanner.

SUMMARY OF THE INVENTION

In accordance with the present invention, there is provided a novel approach for (i) providing the electrical power needed to operate the mobile CT scanner, and (ii) connecting the CT scanner to a workstation, hospital PACs system or other IT network, all without the use of the physical cabling normally associated with a conventional CT scanner.

And there is provided a novel mobile CT machine with cordless and wireless capabilities, such that the novel CT machine does not require physical cabling to (i) provide the electrical power needed to operate the mobile CT scanner, and (ii) connecting the CT scanner to a workstation, hospital PACs system or other IT network.

And there is provided a wireless imaging system which allows scan data to be wirelessly transferred from the imaging system to a surgical guidance system.

In one form of the invention, there is provided a wireless imaging system comprising:

a scanner for creating an image of an interior portion of an object;

a guidance system for using an image of an interior portion of an object to provide guidance to an individual with respect to the object;

the scanner comprising an on-board wireless communication unit, and the guidance system comprising an on-board communication unit, the on-board wireless communication unit of the scanner and the on-board communication unit of the guidance system being configured to wirelessly transfer images created by the scanner directly to the guidance system.

In another form of the invention, there is provided a method for providing images to a guidance system, the method comprising:

providing a wireless imaging system comprising:
a scanner for creating an image of an interior portion of an object;
a guidance system for using an image of an interior portion of an object to provide guidance to an individual with respect to the object;
the scanner comprising an on-board wireless communication unit, and the guidance system comprising an on-board communication unit, the on-board wireless communication unit of the scanner and the on-board communication unit of the guidance system being configured to wirelessly transfer images created by the scanner directly to the guidance system;
creating an image of an interior portion of an object using the scanner; and
wirelessly transferring the image created by the scanner to the guidance system.

In another form of the invention, there is provided an imaging system comprising:
a scanner comprising:
scanning components for creating an image of the interior portion of an object;
an outer cover disposed over the scanning components;
an opening formed in the outer cover; and
a rigid mount which is rigidly mounted to the scanning components and extends through the opening formed in the outer cover.

In another form of the invention, there is provided a method for providing images of an object, the method comprising:
providing a scanner comprising:
scanning components for creating an image of the interior portion of an object;
an outer cover disposed over the scanning components;
an opening formed in the outer cover; and
a rigid mount which is rigidly mounted to the scanning components and extends through the opening formed in the outer cover; and
creating an image of an interior portion of an object using the scanner.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Mobile CT Imaging System in General

Figure 1:
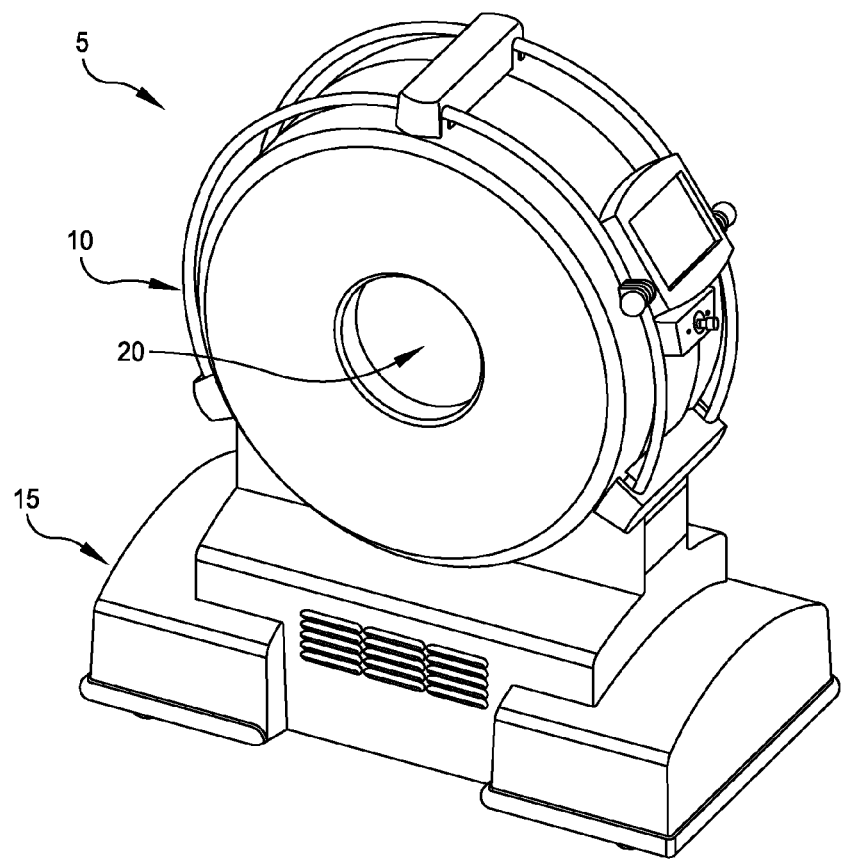
FIGS. 1 and 2 are schematic external views of a novel mobile CT imaging system formed in accordance with the present invention.
Figure 2:
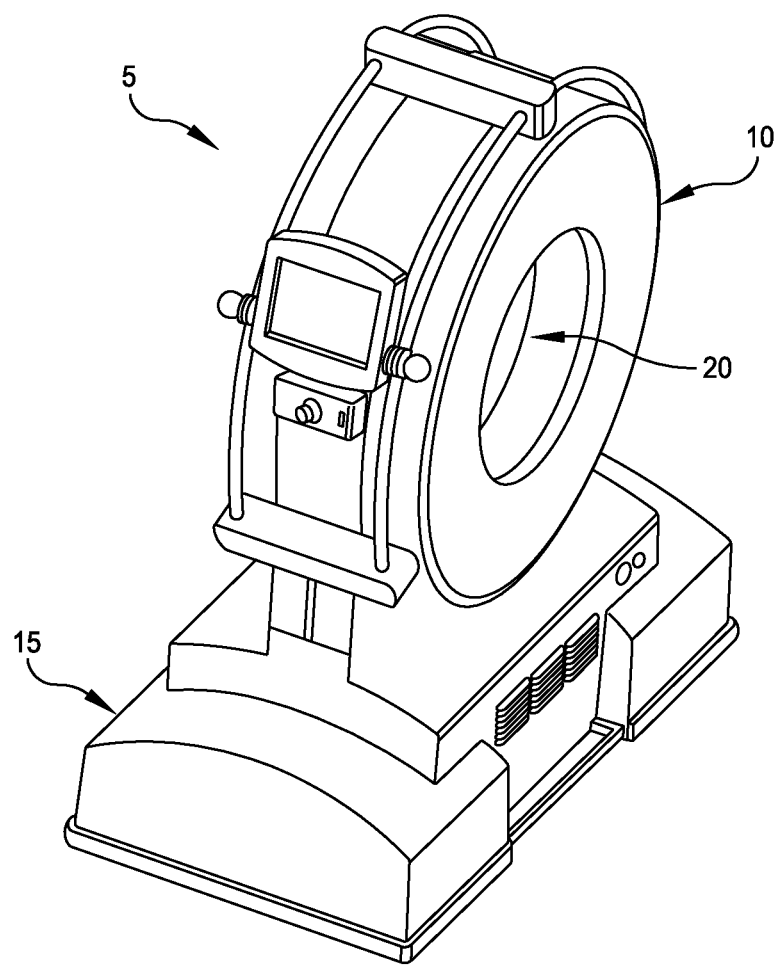

Looking first at FIGS. 1 and 2, there is shown a novel mobile CT imaging system 5 formed in accordance with the present invention. Mobile CT imaging system 5 generally comprises a torus 10 which is supported by a base 15. Torus 10 and base 15 together comprise a frame for mobile CT imaging system 5. A center opening 20 is formed in torus 10. Center opening 20 receives the patient anatomy which is to be scanned, i.e., the head of the patient when mobile CT imaging system 5 is to be used in stroke applications.

Figure 3:
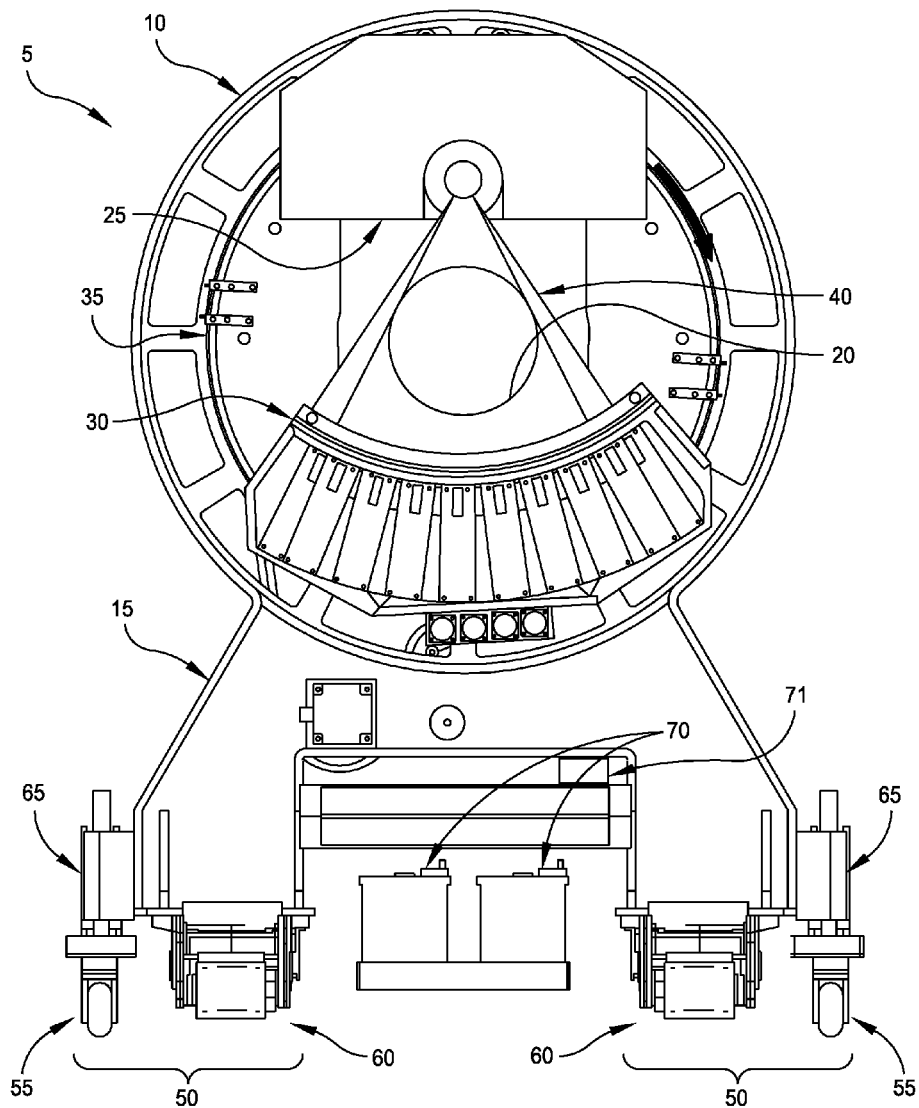
FIG. 3 is a schematic internal view of the novel mobile CT imaging system shown in FIGS. 1 and 2.

Looking next at FIG. 3, torus 10 generally comprises a X-ray tube assembly 25, an X-ray detector assembly 30, and a rotating drum assembly 35. X-ray tube assembly 25 and X-ray detector assembly 30 are mounted to the rotating drum assembly 35 in diametrically-opposing relation, such that the X-ray beam 40 (generated by X-ray tube assembly 25 and detected by X-ray detector assembly 30) is passed through the patient anatomy disposed in center opening 20. Furthermore, since X-ray tube assembly 25 and X-ray detector assembly 30 are mounted on the rotating drum assembly 35 so that they are rotated concentrically about center opening 20, the X-ray beam 40 will be passed through the patient's anatomy along a full range of radial positions, so as to enable the mobile CT imaging system 5 to create the desired computer model of the scanned anatomy.

The various electronic hardware and software for controlling the operation of X-ray tube assembly 25, X-ray detector assembly 30, and rotating drum assembly 35, as well as for processing the acquired scan data so as to generate the desired computer model, may be of the sort well known in the art and may be located in torus 10 and/or base 15.

Still looking now at FIG. 3, base 15 comprises a transport assembly 50 for moving mobile CT imaging system 5 about relative to the patient. More particularly, as disclosed in U.S. Pat. No. 7,397,895, which patent is hereby incorporated herein by reference, transport assembly 50 preferably comprises (i) a gross movement mechanism 55 for moving mobile CT imaging system 5 relatively quickly across room distances, so that the mobile CT imaging system can be quickly and easily brought to the patient, and (ii) a fine movement mechanism 60 for moving the mobile CT imaging system 5 precisely, relative to the patient, during scanning, so that the patient can be scanned without being moved. As discussed in detail in the aforementioned U.S. Pat. No. 7,397,895, gross movement mechanism 55 preferably comprises a plurality of free-rolling casters, and fine movement mechanism 60 preferably comprises a plurality of centipede belt drives (which can be configured for either stepped or continuous motion, whereby to provide either stepped or continuous scanning). Hydraulic apparatus 65 permits either gross movement mechanism 55 or fine movement mechanism 60 to be engaged with the floor, whereby to facilitate appropriate movement of mobile CT imaging system 5. However, as also discussed in detail in the aforementioned U.S. Pat. No. 7,397,895, gross movement mechanism 55 may be omitted entirely, and only fine movement mechanism 60 may be provided, in which case fine movement mechanism 60 is used to both (i) move mobile CT imaging system 5 to the patient prior to scanning, and (ii) move the mobile CT imaging system relative to the patient during scanning.

Mobile CT imaging system 5 also comprises cordless and wireless capabilities, such that the mobile CT imaging system 5 does not require physical cabling to (i) provide the electrical power needed to operate the mobile CT imaging system 5, and (ii) connecting the mobile CT imaging system 5 to a workstation, hospital PACs system or other IT network.

More particularly, and as will hereinafter be discussed in further detail below, mobile CT imaging system 5 also comprises a novel on-board power unit 70 for providing the electrical power needed to operate the mobile CT imaging system 5 without requiring the use of conventional physical cabling during the same, and a novel on-board networking unit 71 for connecting the mobile CT imaging system 5 to a workstation, hospital PACs system or other IT network without requiring the use of conventional physical cabling during the same.

On-Board Power Unit 70

As noted above, and looking now at FIGS. 3 and 4, mobile CT imaging system 5 comprises an on-board power unit 70 for providing the electrical power needed to operate the mobile CT imaging system 5 without requiring the use of conventional physical cabling during the same. The provision of such an on-board power unit 70 has been heretofore unnecessary, inasmuch as conventional CT scanners are fixed-position devices which can have their power cabling carefully arranged at the time of CT scanner installation so as to make the power cabling relatively inobtrusive (e.g., the power cabling can be carefully positioned so that it is out of the way of patients and medical personnel). However, mobile CT imaging system 5 is intended to be quickly and easily deployed in critical-care situations where there is seldom time to carefully arrange the power cabling so as to keep it out of the way. Thus, the creation of a mobile CT imaging system 5 has now created the need for a novel on-board power unit 70 for providing the electrical power needed to operate the mobile CT imaging system 5 without requiring the use of conventional physical cabling during the same. On-board power unit 70 is designed to address this need.

Figure 4:
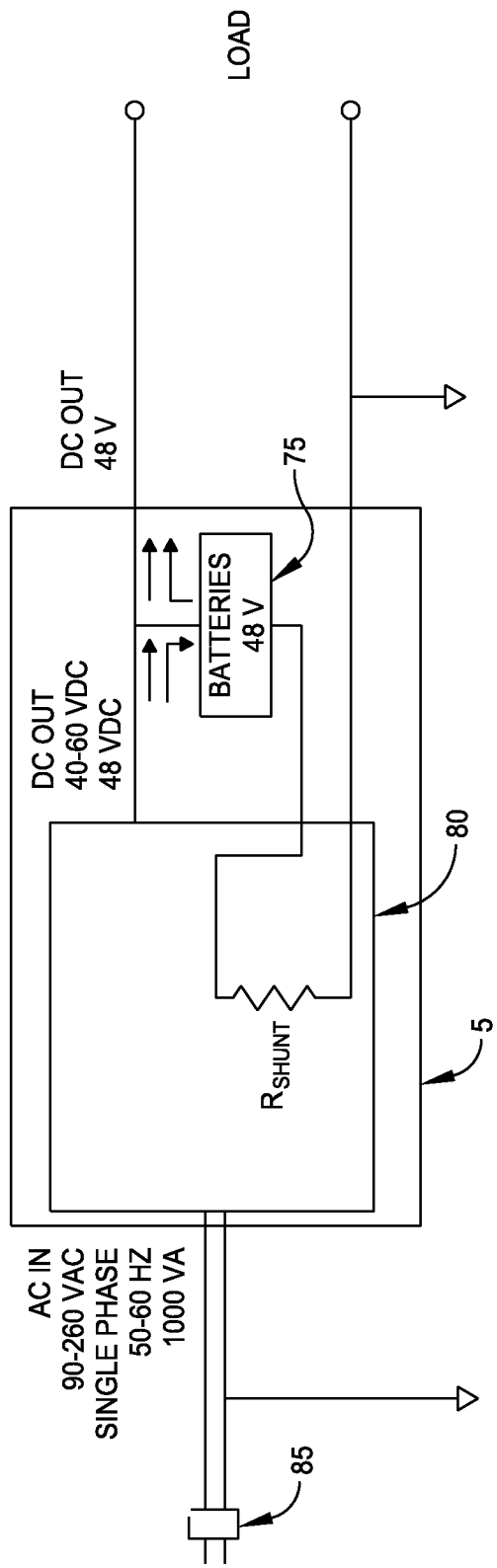
FIG. 4 is a schematic view showing a novel on-board power unit for providing the electrical power needed to operate the mobile CT imaging system without requiring the use of conventional physical cabling during the same.

Looking now at FIG. 4, on-board power unit 70 comprises one or more batteries 75 configured to output the electrical power needed to operate mobile CT imaging system 5. In one preferred form of the invention, mobile CT imaging system 5 requires 48 V DC, and batteries 75 comprises four 12 V batteries. Batteries 75 are preferably of the sort well known in the art.

On-board power unit 70 also comprises a transformer/charger 80. Transformer/charger 80 is constructed so that when the on-board power unit's plug 85 is plugged into a standard wall outlet, transformer/charger 80 will charge batteries 75. By way of example but not limitation, transformer/charger 80 may be configured to take 90-260 V, single phase, 50-60 Hertz AC power and convert it to 48 V DC power. Thus, between uses, mobile CT imaging system 5 may be positioned next to a standard wall outlet and plug 85 used, in conjunction with transformer/charger 80, to charge batteries 75. When mobile CT imaging system 5 is thereafter to be used, plug 85 is unplugged from the wall outlet, and then the mobile CT imaging system 5 is moved (i.e., using transport assembly 50) to the patient for scanning.

In some circumstances it may be acceptable to use mobile CT imaging system 5 while plug 85 is plugged into a standard wall outlet. To this end, on-board power unit 70 is also configured so that when plug 85 is plugged into a wall outlet, mobile CT imaging system 5 will draw power directly from transformer/charger 80, with or without also drawing power out of batteries 75.

On-board power unit 70 is mounted to the frame of mobile CT imaging system 5 so that the on-board power unit 70 will move with the remainder of the system. In one preferred form of the invention, on-board power unit 70 is mounted in base 15.

On-Board Networking Unit 71

As noted above, and looking now at FIGS. 3 and 5, mobile CT imaging system 5 comprises a novel on-board networking unit 71 for connecting the mobile CT imaging system 5 to a workstation, hospital PACs system or other IT network without requiring the use of conventional physical cabling during the same.

The provision of such an on-board networking unit 71 has been heretofore unnecessary, inasmuch as conventional CT scanners are fixed-position devices which can have their network cabling carefully arranged at the time of CT scanner installation so as to make the network cabling relatively inobtrusive (e.g., the network cabling can be carefully positioned so that it is out of the way of patients and medical personnel). However, mobile CT imaging system 5 is intended to be quickly and easily deployed in critical-care situations where there is seldom time to carefully arrange the network cabling so as to keep it out of the way. Thus, the creation of a mobile CT imaging system 5 has now created the need for a novel on-board networking unit 71 for connecting the mobile CT imaging system 5 to a workstation, hospital PACs system or other IT network without requiring the use of conventional physical cabling during the same.

Figure 5:
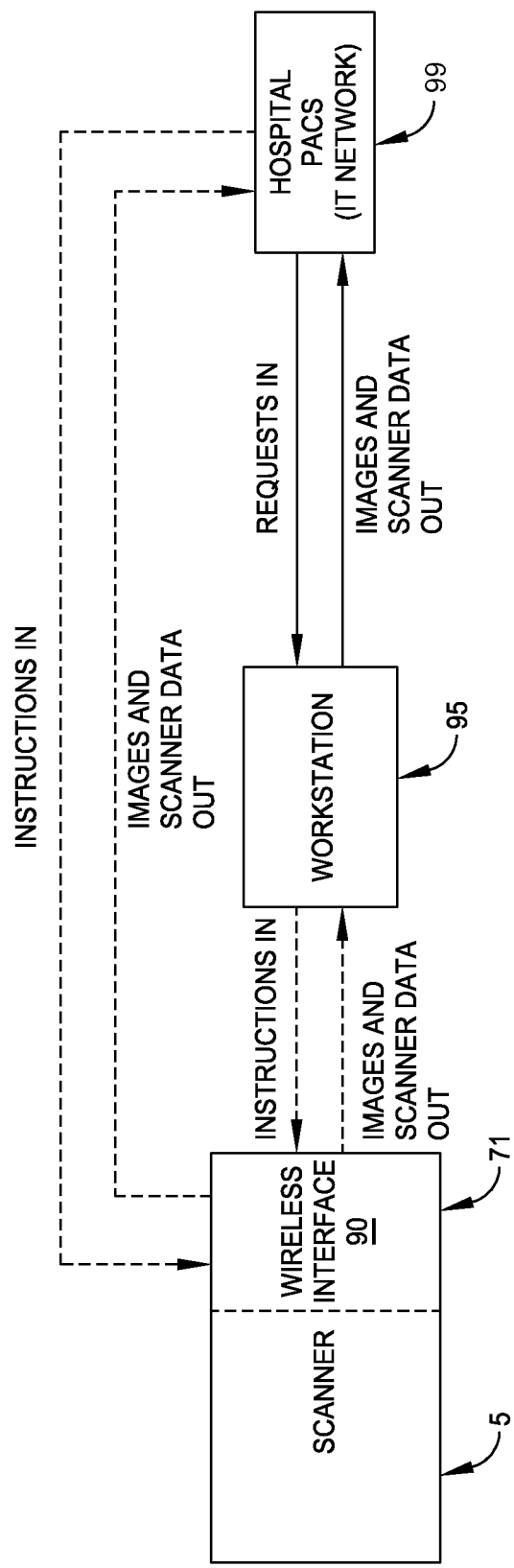
FIG. 5 is a schematic view showing a novel on-board networking unit for connecting the mobile CT imaging system to a workstation, hospital PACs system or other IT network without requiring the use of conventional physical cabling during the same.

Looking now at FIG. 5, on-board networking unit 71 comprises a wireless interface 90 configured to wirelessly connect mobile CT imaging system 5 to a workstation 95, whereby to permit medical personnel to issue scanning instructions to mobile CT imaging system 5 using the workstation 95, and whereby to enable the mobile CT imaging system 5 to send images and scanner data to the workstation 95 for viewing by medical personnel. Workstation 95 can, in turn, be connected to a hospital PACs system or other IT network 99, so as to permit mobile CT imaging system 5 to be controlled from remote locations and so as to permit images and scanner data to be viewed by medical personnel at remote locations. Alternatively, wireless interface 90 can be directly connected to the hospital PACs system or other IT network 99.

Wireless interface 90 is preferably of the sort well known in the art, e.g., a WIFI interface conforming to appropriate IEEE standards such as 802.11b, 802.11g, etc.

On-board networking unit 71 is mounted to the frame of mobile CT imaging system 5 so that the on-board networking unit 71 will move with the remainder of the system. In one preferred form of the invention, on-board networking unit 71 is mounted in base 15.

Use

Mobile CT imaging system 5 is preferably used as follows.

When not in use, mobile CT imaging system 5 is preferably stored in the emergency room (or other intended place of use), in an out-of-the-way location, raised on its gross movement mechanism 55 (i.e., its casters), and with its plug 85 plugged into a standard wall outlet so that batteries 75 are fully charged.

When a patient arrives at the emergency room presenting stroke-like symptoms, the patient is quickly scanned in the emergency room, on their gurney, using mobile CT imaging system 5. More particularly, mobile CT imaging system 5 is unplugged from the wall, and the mobile CT imaging system 5 is then moved on its casters to the patient, so that the patient (while still lying on their gurney) is positioned within the center opening 20 of mobile CT imaging system 5. Thereafter, using on-board power unit 70, hydraulic apparatus 65 is activated so that mobile CT imaging system 5 is supported on its fine movement mechanism 60 (i.e., the centipede belt drives). Using on-board power unit 70 and on-board networking unit 71, scanning is then commenced, with fine movement mechanism 60 precision-advancing mobile CT imaging system 5 relative to the patient during scanning. Image data is off-loaded (to work station 95, and/or the hospital PACs system or other IT network 99 using on-board networking unit 71.

Thus, with the present invention, there is provided a novel mobile CT imaging system 5 with cordless and wireless capabilities, such that the novel mobile CT imaging system 5 does not require physical cabling to (i) provide the electrical power needed to operate the mobile CT imaging system 5, and (ii) connecting the mobile CT imaging system 5 to a workstation 95, hospital PACs system or other IT network 99.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines which are used to scan inanimate objects. Furthermore, the present invention may be used with non-CT-type imaging systems. In essence, the present invention has application to any mobile imaging device which requires cordless and wireless operation.

Wireless Imaging System

In the foregoing document, there is disclosed a mobile imaging system (e.g., a mobile CT machine) equipped with cordless and wireless capabilities.

Among other things, the mobile imaging system comprises an on-board power unit which is adapted to provide the electrical power needed to operate the imaging system, whereby to eliminate the need to run power cables from a wall plug to the mobile imaging system while the imaging system is scanning a patient. This greatly enhances the utility of the mobile imaging system, since it means that scanning can occur without regard to the location of wall plugs, and power cables do not need to extend from a wall plug to the imaging system while it is imaging a patient, which could interrupt diagnosis and/or treatment workflow around the patient due to the presence of the power cables.

And among other things, the mobile imaging system also comprises an on-board networking unit which is adapted to wirelessly connect the imaging system to a workstation, or to a hospital PACS system (i.e., a hospital Picture Archiving And Communication System), or to some other IT network, etc., whereby to eliminate the need to run data cables from the mobile imaging system to a wall jack. Again, this greatly enhances the utility of the mobile imaging system, since it means that images can be sent from the imaging system to another device or system without regard to the location of wall jacks, and data cables do not need to extend from the mobile imaging system to a wall jack, particularly while it is imaging a patient, which could interrupt diagnosis and/or treatment workflow around the patient due to the presence of the data cables.

In another aspect of the invention, a mobile imaging system equipped with an on-board networking unit for wirelessly connecting the imaging system to a workstation, a hospital PACS system (i.e., a hospital Picture Archiving And Communication System), some other IT network, etc. may be advantageously used in conjunction with a surgical guidance system (e.g., a surgical navigation system, a surgical robotics system, a surgical planning system, and/or any other system utilizing image data to provide guidance during a medical procedure, e.g., real-time DICOM images to provide real-time guidance during a surgical procedure). In this respect it will be appreciated that the provision of a mobile imaging system equipped with cordless and wireless capabilities is particularly well suited to use in an operating room, whereby to provide intraoperative imaging for a patient undergoing a procedure.

Figure 6:
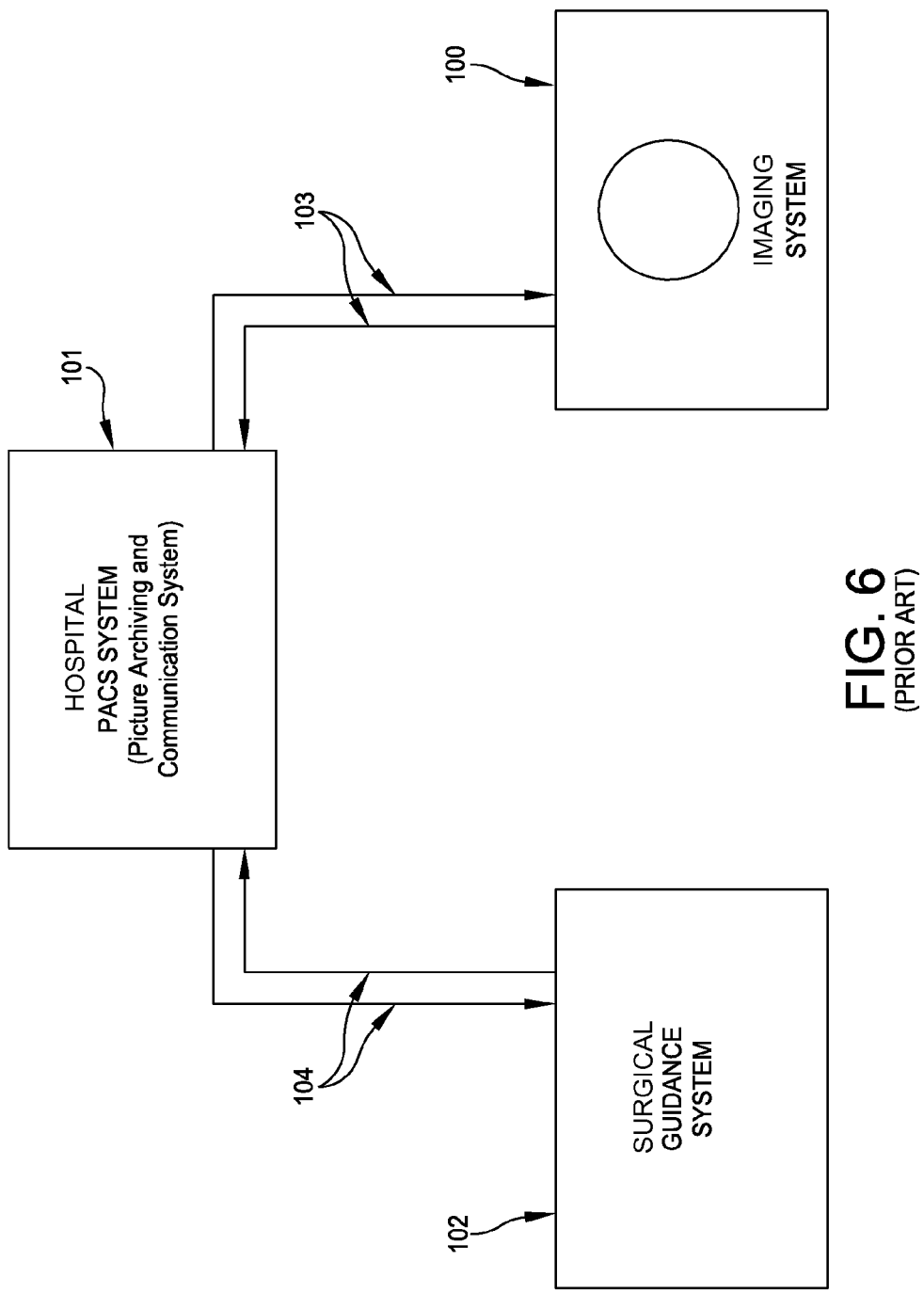
FIG. 6 is a schematic view showing a conventional way for linking a scanner system to a guidance system via a PACS system.

More particularly, FIG. 6 shows a typical conventional approach for connecting an imaging system 100 (e.g., a fixed-position CT machine), a hospital PACS system 101 and a surgical guidance system 102 (e.g., a surgical navigation system). In this conventional approach, the imaging system 100 (e.g., the fixed-position CT machine) is connected (e.g., with data cables 103) to the hospital PACS system 101, and the surgical guidance system 102 (e.g., a surgical navigation system) is connected (e.g., with data cables 104) to the hospital PACS system 101. In use, the imaging system 100 (e.g., the fixed-position CT machine) is typically employed sometime prior to the surgery (e.g., the night before the surgery) to image the anatomy which is to be operated on. The images from the imaging system 100 (e.g., the fixed-position CT machine) are sent from the imaging system 100 (e.g., the fixed-position CT machine) to the hospital PACS system 101 (e.g., by data cables 103) for storage. At the time of surgery, the surgical guidance system 102 retrieves (e.g, by data cabling 104) the stored images from the hospital PACS system 101 and, using fiducial markers positioned on the anatomy at the time of imaging (and hence included in the images), or using anatomical landmarks easily located on the anatomy and on the images, places the images "into registration" with the surgical guidance system 102 and the anatomy, so that the images which were previously obtained by the imaging system 100 (e.g., the fixed-position CT machine) can be used by the surgical guidance system 102 (e.g., a surgical navigation system, a surgical robotics system, a surgical planning system, and/or any other system utilizing image data such as DICOM images to provide guidance) during the actual surgery. Alternatively, images from the imaging system 100 (e.g., the fixed-position CT machine) or the hospital PACS system 101 may be transferred to the surgical guidance system 102 using physical media (e.g., CD, DVD, USB key, etc.).

While this approach is effective and is currently in widespread use, it puts a substantial strain on the IT network of the hospital, including the hospital PACS system 101, since images from the imaging system 100 (e.g., the fixed-position CT machine) must be:

(i) transferred from the imaging system 100 (e.g., the fixed-position CT machine) to the hospital PACS system 101;

(ii) stored on the hospital PACS system 101 until the time of surgery; and (iii) transferred from the hospital PACS system 101 to the surgical guidance system 102 at the time of surgery.

In this respect it will be appreciated that the images being transferred from the imaging system 100 (e.g., the fixed-position CT machine) to the hospital PACS system 101, and from the hospital PACS system 101 to the surgical guidance system 102, are typically large data files which consume significant system resources, particularly within the hospital PACS system 101. Furthermore, there can be substantial delays while waiting for images to be transferred from the imaging system 100 (e.g., the fixed-position CT machine) to the hospital PACS system 101, and/or from the hospital PACS system 101 to the surgical guidance system 102, which can result in delays before and during surgery. This is particularly problematic when the delays occur intraoperatively.

Alternatively, images from the imaging system 100 (e.g., the fixed-position CT machine) or the hospital PACS system 101 may be transferred to the surgical guidance system 102 using physical media (e.g., CD, DVD, USB key, etc.). However, this approach is both time-consuming and inconvenient.

Figure 7:
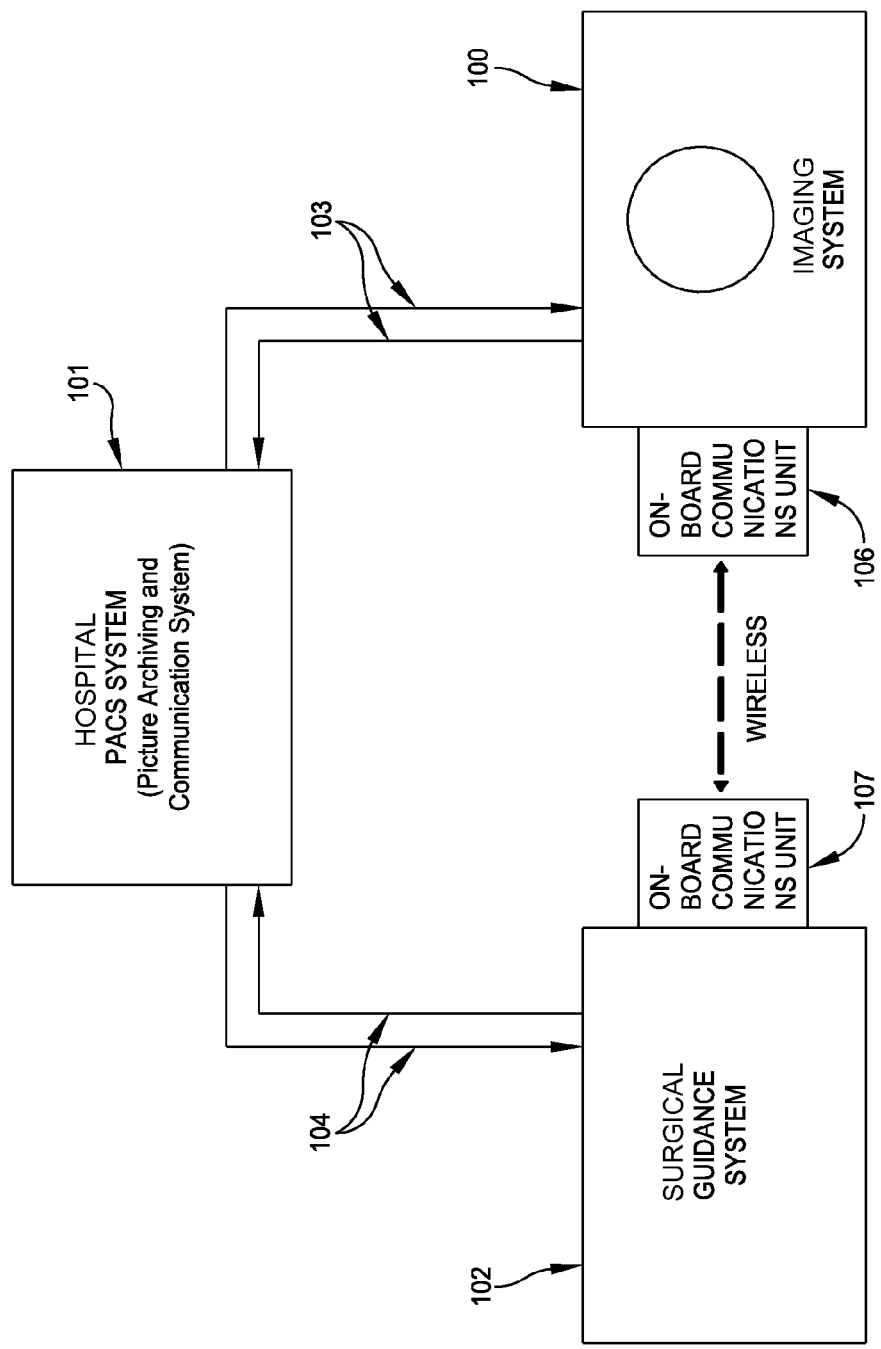
FIG. 7 is a schematic view showing a novel method for wirelessly linking a scanner system to a guidance system.

In accordance with the present invention, and looking now at FIG. 7, the wireless capability of mobile CT imaging system 5 (see above) can be harnessed to send images from the mobile CT imaging system 5 directly to the surgical guidance system 102, thereby completely sidestepping the hospital PACS system 101 at the time of image transmission, and/or eliminating the need for the use of physical storage media (e.g., CD, DVD, USB key, etc.) to transfer the images from mobile CT imaging system 5 and/or the hospital PACS system 101 to surgical guidance system 102. In this form of the invention, imaging system 100 (e.g., mobile CT imaging system 5) comprises an on-board communications unit 106 (e.g., the on-board networking unit 71 of mobile CT imaging system 5), and surgical guidance system 102 comprises an on-board communications unit 107, wherein the on-board communications unit 106 of imaging system 100 is configured to wirelessly communicate with the on-board communications unit 107 of surgical guidance system 102, whereby to enable the exchange of data, e.g., images, computer models, etc., therebetween. As a result, images from imaging system 100 (e.g., mobile CT imaging system 5) can be delivered to the surgical guidance system 102 more quickly, which can be of significant advantage when performing a surgical procedure with the surgical guidance system 102. In addition, since such image transmissions completely sidestep the hospital PACS system 101, the load on the IT network of the hospital, and particularly the load on the hospital PACS system 101, is significantly reduced. Of course, it is anticipated that the images captured by mobile CT imaging system 5 will still be forwarded to the hospital PACS system 101 at some point for archiving (e.g., via data cables 103), but this may be done at a time when the load on the IT network of the hospital, and particularly the load on the hospital PACS system 101, is reduced, e.g., at night.

Significantly, the present invention is particularly advantageous where scanning is done intraoperatively (e.g., with a mobile CT imaging system 5 having cordless and wireless capabilities and being physically located in the operating room), and real-time imaging data needs to be transferred from the imaging system 100 (e.g., the mobile CT imaging system 5) to the surgical guidance system 102 (e.g., a surgical navigation system, a surgical robotics system, a surgical planning system, and/or any other system utilizing image data such as DICOM images to provide guidance).

It should also be appreciated that, if desired, the surgical guidance system 102 (e.g., a surgical navigation system, a surgical robotics system, a surgical planning system, and/or any other system utilizing image data to provide guidance) can also pull images from the hospital PACS system 101 if desired (e.g., via data cables 104), which allows multiple imaging modalities to be fused within the surgical guidance system 102. By way of example but not limitation, where the imaging system 100 comprises a mobile cordless, wireless CT imaging system 5 (or another CT imaging system equipped with wireless communications) which is present in the operating room, the surgical guidance system 102 can also pull images created by other imaging modalities (e.g., MRI, PET, SPECT, ultrasound, etc.) from the hospital PACS system 101 so that images from multiple modalities are available to the surgical guidance system 102. Alternatively, where imaging system 100 comprises an MRI machine which is present in the operating room, the surgical guidance system 102 can also pull images created by other imaging modalities (e.g., CT, PET, SPECT, ultrasound, etc.) from hospital PACS system 101, so that images from multiple modalities are available to the surgical guidance system 102.

If desired, imaging system 100 can pull image data out of the hospital PACS system 101 and wirelessly send that image data to surgical guidance system 102.

With respect to the foregoing, it should be appreciated that the present invention is applicable to substantially any type of imaging system equipped with wireless communication capabilities, e.g., a mobile CT machine, a fixed-position CT machine, an MRI machine, an ultrasound machine, a SPECT machine, a PET machine, an X-ray machine, etc.

In one preferred form of the invention, the imaging system of the present invention comprises the CERETOM® mobile CT imaging system and/or the BODYTOM® mobile CT imaging system manufactured by NeuroLogica Corporation of Danvers, Massachusetts.

In one preferred form of the invention, the imaging system 100 (e.g., mobile CT imaging system 5) is connected to the surgical guidance system 102 using a Wireless IEEE 802.11 a/b/g/n transfer protocol, with the connection being configured as either an ad-hoc point-to-point network or as access points through a router. In another preferred form of the invention, the imaging system 100 (e.g., mobile CT imaging system 5) is connected to the surgical guidance system 102 using Bluetooth, Infrared (IR) or other communication apparatus and/or protocols. The image transfer syntax is compliant with the DICOM 3.1 standard for medical image transfer and/or other industry standards.

Non-Medical Applications

In the preceding discussion, the present invention is discussed in the context of medical applications, e.g., scanning anatomy in order to provide a physician with information about that anatomy and/or to provide images to a surgical guidance system whereby to provide surgical guidance to a physician during a surgical procedure. However, it is also possible to use the present invention in non-medical applications, e.g., to scan objects for security purposes (such as luggage, handbags, backpacks, packages, shipping containers, etc. at an airport security station, etc.) and/or to provide images to an operational guidance system whereby to provide operational guidance to a user during an operational procedure (such as remote bomb deactivation, etc).

Rigid, Gantry-Mounted Fiducial Markers

In recent years, surgical guidance systems (e.g., a surgical navigation system, a surgical robotics system, a surgical planning system, and/or any other system utilizing images to provide guidance to a physician during a medical procedure) have become more commonplace in the operating room. In general, surgical guidance systems use computer technology for directing and/or performing surgical procedures. This is done by first creating an accurate computer model of the anatomy which is to be operated on, and then using the computer model, in conjunction with tracked instruments, to carry out the surgical procedure, e.g., to guide manual surgery by providing the surgeon with visual and/or audio cues for guidance during the surgery, and/or to actually perform the surgery via electromechanical drivers (e.g., a robotic system) which move the tracked instruments during the surgery, with the surgeon retaining manual override control of the tracked instruments. In any case, surgical guidance systems require the creation of an accurate computer model of the anatomy which is to be operated on.

The computer model of the anatomy can be created using a variety of imaging systems including CT, MRI, PET, SPECT, X-rays, ultrasound, etc., with the final objective being the creation of a 3D model of the anatomy using the images created by the imaging system. In general, a CT imaging system is preferred for many procedures. The images generated by the imaging system, and/or the computer models created from the images generated by the imaging system, may be stored in a hospital PACS system (i.e., a hospital Picture Archiving And Communication System) for subsequent access by the surgical guidance system.

More particularly, FIG. 6 shows a typical conventional approach for generating images and/or computer models with an imaging system 100 (e.g., a CT imaging system), storing those images and/or computer models in a hospital PACS system 101, and then transferring those images and/or computer models to a surgical guidance system 102 for use during a surgical procedure. In this conventional approach, the imaging system 100 (e.g., a CT imaging system) is typically used to scan the anatomy the day before (or the day of) the surgery so as to image the anatomy which is to be operated on. The images from imaging system 100 (e.g., a CT imaging system), and/or the computer models generated by the imaging system 100 (e.g., a CT imaging system) are sent from the imaging system 100 (e.g., the CT imaging system) to the hospital PACS system 101 for storage. At the time of surgery, the surgical guidance system 102 retrieves the stored images and/or computer models from the hospital PACS system 101 and, using fiducial markers positioned on the anatomy at the time of imaging (and hence included in the images and/or computer models stored in the hospital PACS system 101), or using anatomical landmarks easily located on the anatomy and on the images and/or computer models, places the images and/or computer models "into registration" with the surgical navigation system 102 and the anatomy, so that the images and/or computer models which were previously generated by the imaging system 100 can be used to guide the surgical guidance system 102 during the actual surgery.

While this approach is effective and is currently in widespread use, it relies on the use of images and/or computer models which were generated in advance of the surgery. In some circumstances (e.g., where the anatomy is substantially rigid and unchanging, such as slow-growing bone), this approach can be satisfactory. However, in other circumstances (e.g., where the anatomy is not rigid, and/or where the anatomy is fast-growing), this approach may not be satisfactory, particularly where the surgery is delicate and precision must be measured in millimeters (e.g., brain surgery). The use of images and/or computer models which were made in advance of the actual surgery is particularly unsatisfactory where the anatomy changes during the surgery itself, e.g., where tissue is shifted and/or removed during surgery, in which case the pre-surgery images and/or computer model may be completely useless. By way of example but not limitation, in many brain surgeries, the brain may shift once the skull is opened, thereby rendering the pre-surgery images and/or computer model inaccurate and unreliable.

To this end, it has been recognized that it is possible to provide an imaging system 100 in the operating room, so as to created real-time images and/or computer models of the anatomy which is being operated on. Furthermore, it has also been recognized that, by providing fiducial markers on the imaging system 100 itself, it can be possible to automatically place the images and/or computer models generated by the imaging system 100 into proper registration with the surgical guidance system 102 and the anatomy, so that the real-time images and/or computer models from the imaging system 100 can be used by the surgical guidance system 102 during the surgery. See, for example, FIG. 8, which shows an imaging system 100 (e.g., mobile CT imaging system 5) with fiducial markers 105 placed thereon. The locations of these fiducial markers are detected by appropriate detectors associated with surgical guidance system 102, e.g., the detectors 108 shown in FIG. 8.

Figure 8:
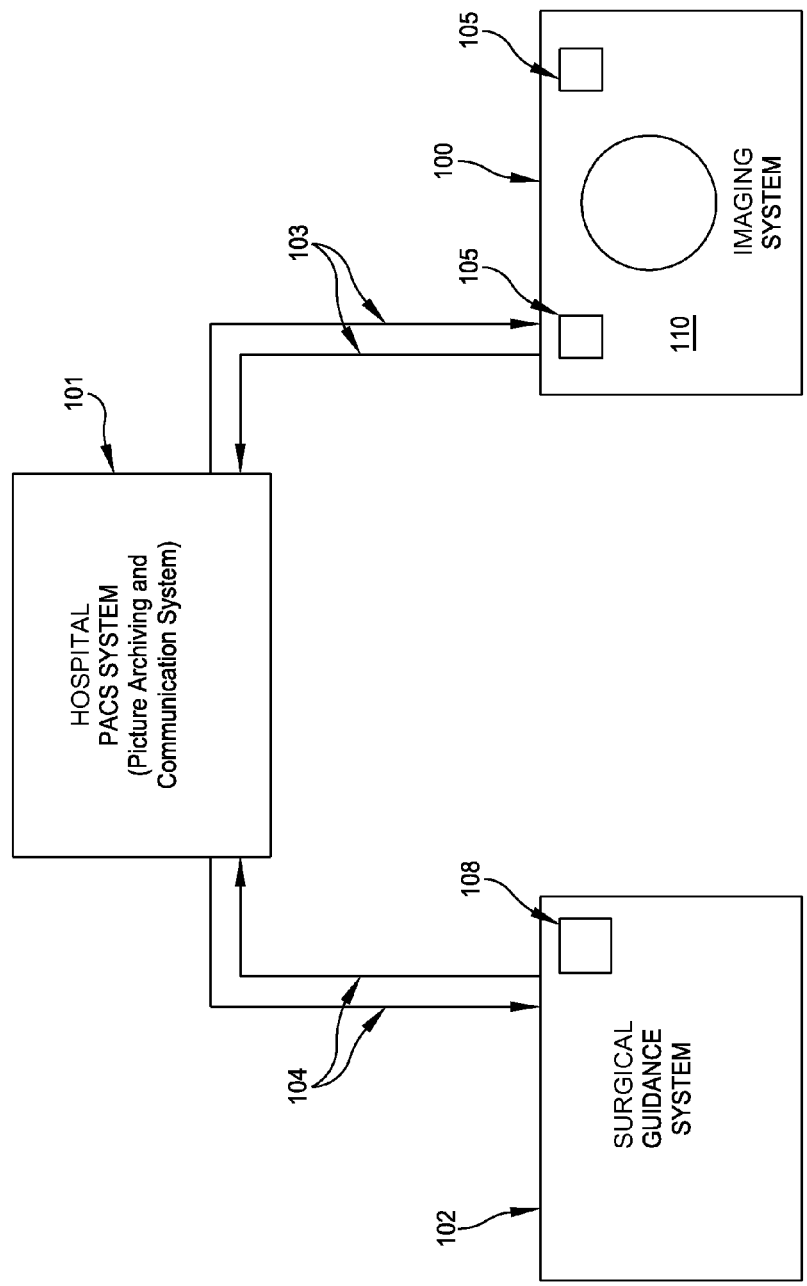
FIG. 8 is a schematic view showing a prior art system wherein fiducial markers are mounted to the outer cover of the imaging system so as to be "visible" to the guidance system.
Figure 9:
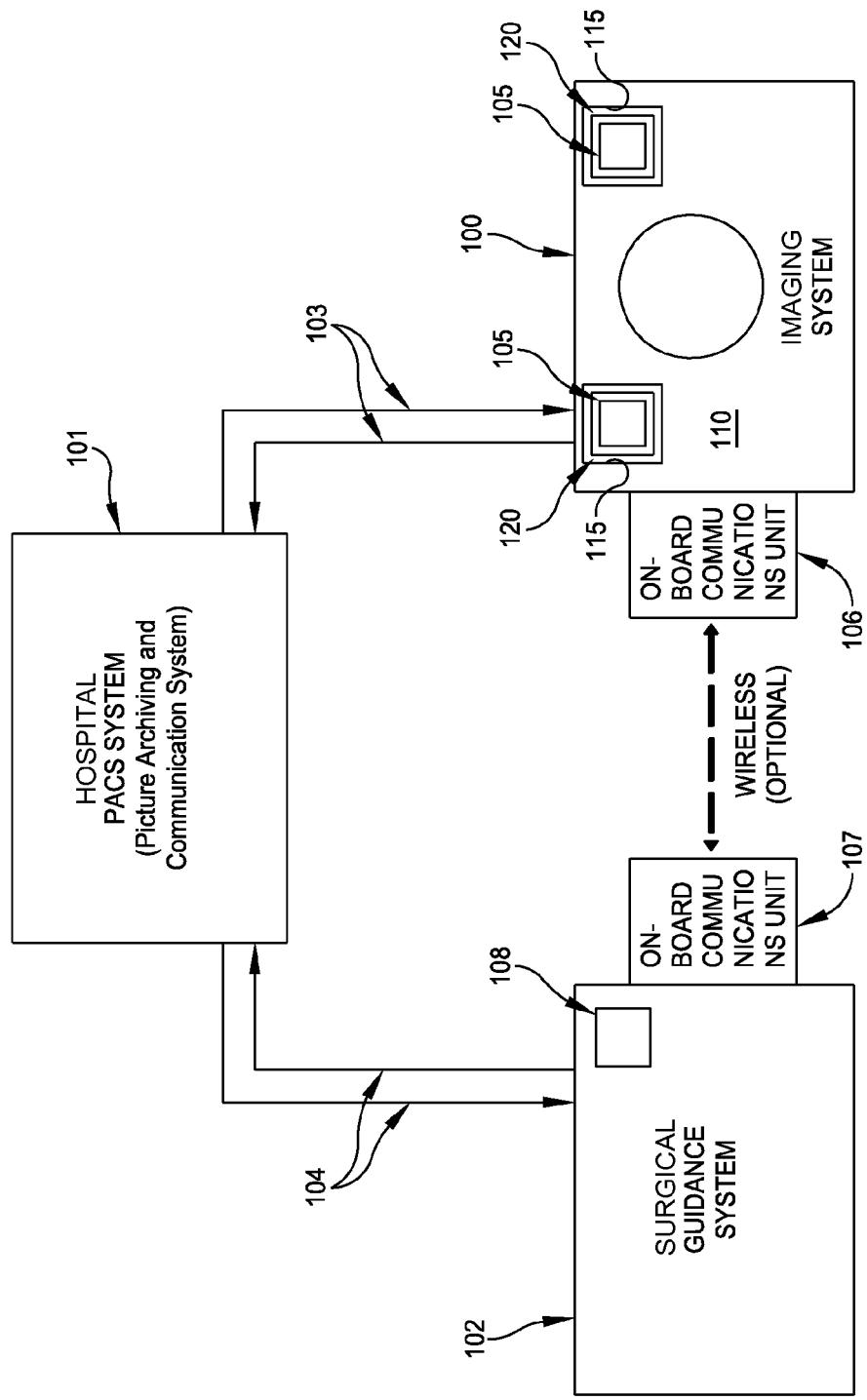
FIG. 9 is a schematic view showing a novel system wherein fiducial markers are secured to a rigid mount which is rigidly mounted to the scanning components of the imaging system, and wherein the rigid mount extends through the outer cover of the imaging system so that the fiducial markers are "visible" to the guidance system.

Unfortunately, while the system shown in FIG. 8 works, in practice, it is characterized by limited resolution. This is because the fiducial markers 105 placed on the imaging system 100 (e.g., mobile CT imaging system 5), which typically work via IR (infrared) detection, RF (radio-frequency) detection, etc., are attached to the outer cover 110 of the imaging system 100 (e.g., mobile CT imaging system 5) so that they can be detected by the surgical guidance system 102. However, the outer cover 110 of the imaging system 100 (e.g., mobile CT imaging system 5) is typically a light cover of sheet metal or plastic which can move relative to the scanning components of the imaging system 100, either during operation of the imaging system 100, during transport of the imaging system 100, and/or during maintenance of the imaging system 100 (when outer cover 110 may be dismounted from, and then re-mounted to, the imaging system 100). As a result, the fiducial markers 105 attached to the outer cover 110 of the imaging system 100 can move relative to the scanning components of the imaging system 100, and hence it is not possible to provide highly accurate registration of the images and/or computer models from the imaging system 100 with the surgical guidance system 102 and the anatomy without constant re-calibration of the system. While this approach may be acceptable for certain types of surgery which require real-time images and/or computer models and which are not spatially critical, it may not be acceptable for other types of surgery which are spatially critical (e.g., brain surgery).

To this end, in accordance with the present invention, and looking now at FIGS. 9-13, there is provided an improved imaging system 100 for providing substantially real-time images and computer models of the anatomy being operated on, and placing those images into highly accurate registration with the surgical guidance system 102 and the anatomy. More particularly, with the present invention, one or more openings 115 are formed in outer cover 110 of the imaging system 100, and one or more rigid mounts 120 are connected to the scanning components of the imaging system 100 and extend out through the openings 115 in outer cover 110. The fiducial markers 105 are attached to the outboard ends of the rigid mounts 120 so that the fiducial markers 105 do not move relative to the scanning components of the imaging system 100 (e.g., during operation of the imaging system 100, during transport of the imaging system 100, and/or during maintenance of the imaging system 100). As a result, by rigidly mounting fiducial markers 105 in this manner to the scanning components of the imaging system 100, real-time images and computer models of the anatomy can be provided, and those images and computer models can be placed into highly accurate registration with the surgical guidance system 102 and the anatomy.

If desired, a fiducial marker 105 may be provided as part of an array of fiducial markers, and the array of fiducial markers may be mounted to the imaging system 100 by mounting the array of fiducial markers to a plurality of rigid mounts 120.

With respect to the foregoing, it should be appreciated that the present invention is applicable to substantially any type of imaging system, e.g., a mobile CT machine such as mobile CT imaging system 5, a fixed-position CT imaging system, an MRI machine, an ultrasound machine, a SPECT machine, a PET machine, an X-ray machine, etc.

Figure 10:
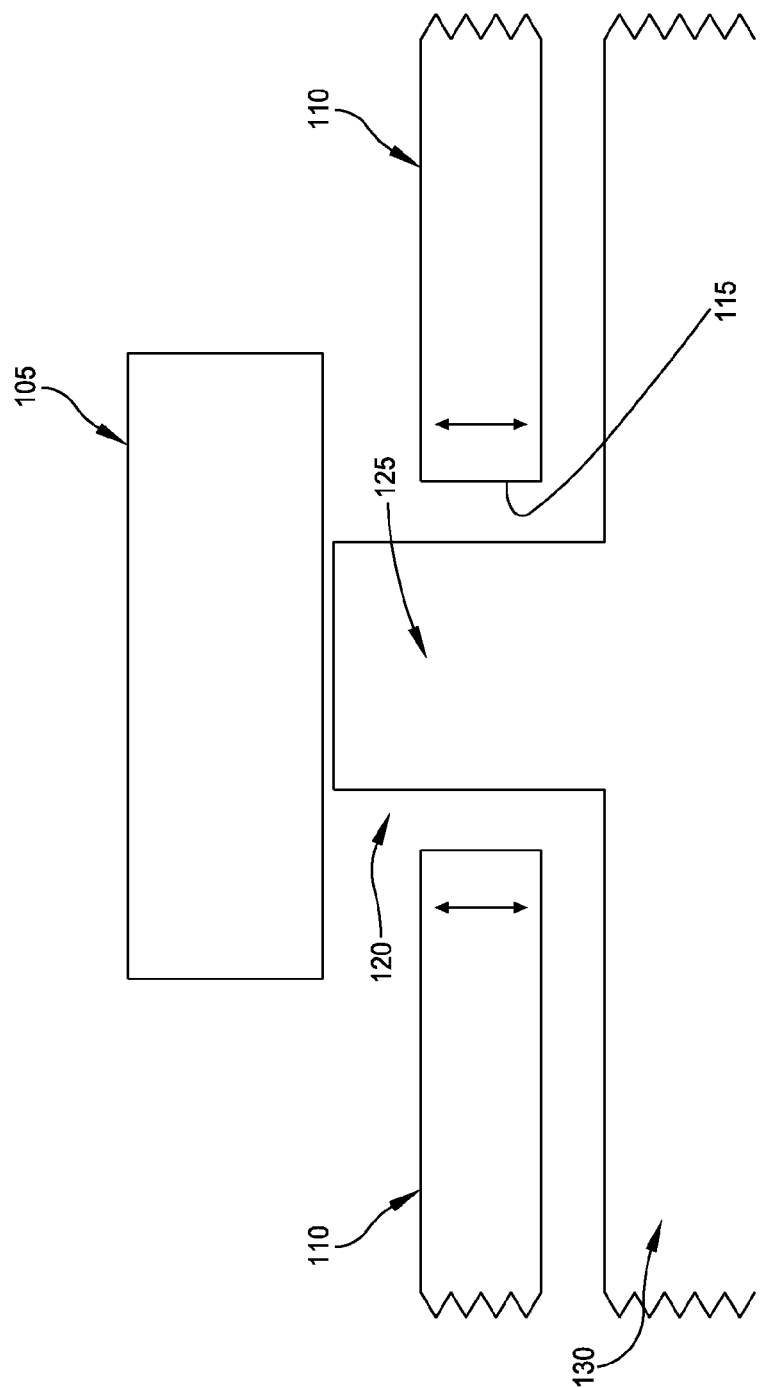
FIG. 10 is a schematic sectional view showing a fiducial marker secured to a rigid mount and visible to the guidance system.
Figure 11:
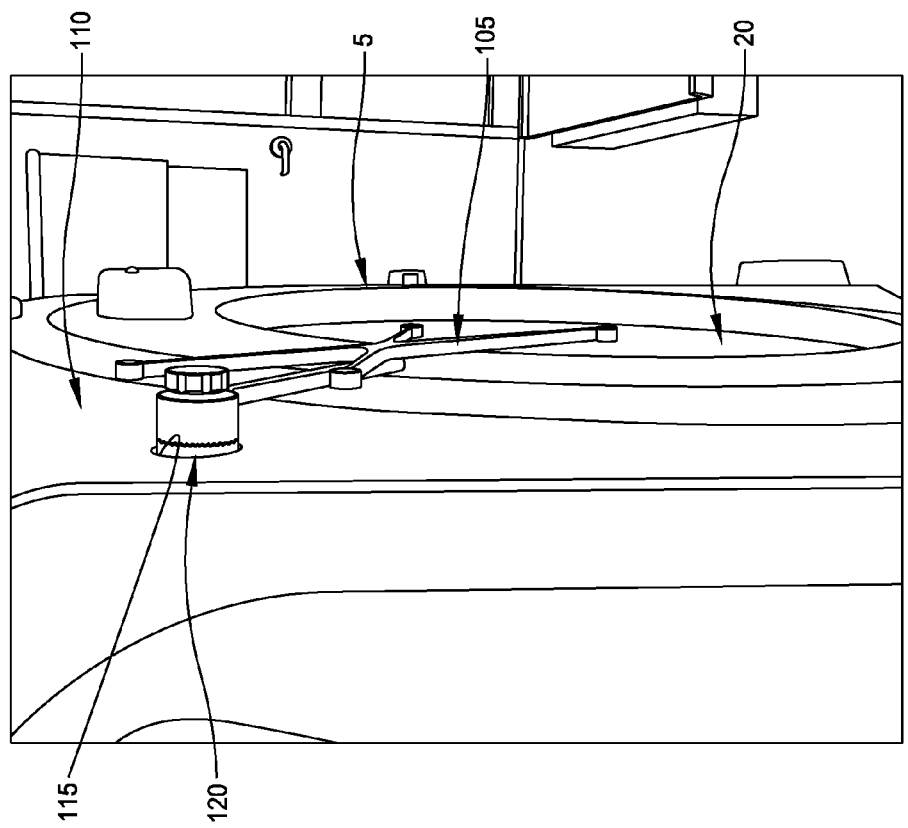
FIG. 11 is a schematic view showing a fiducial marker secured to a rigid mount which extends through the outer cover of the imaging system.
Figure 12:
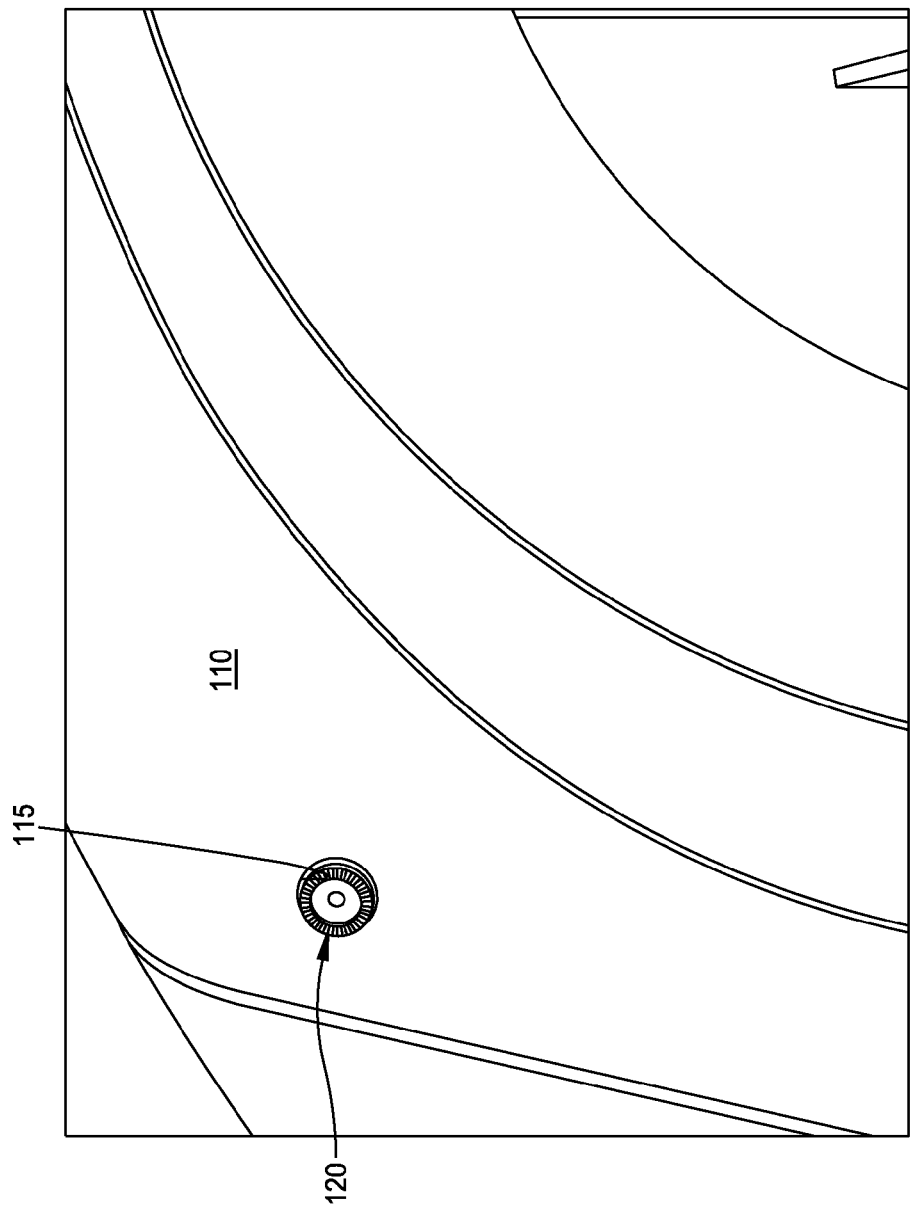
FIG. 12 is a schematic view showing a rigid mount extending through the outer cover of the imaging system.
Figure 13:
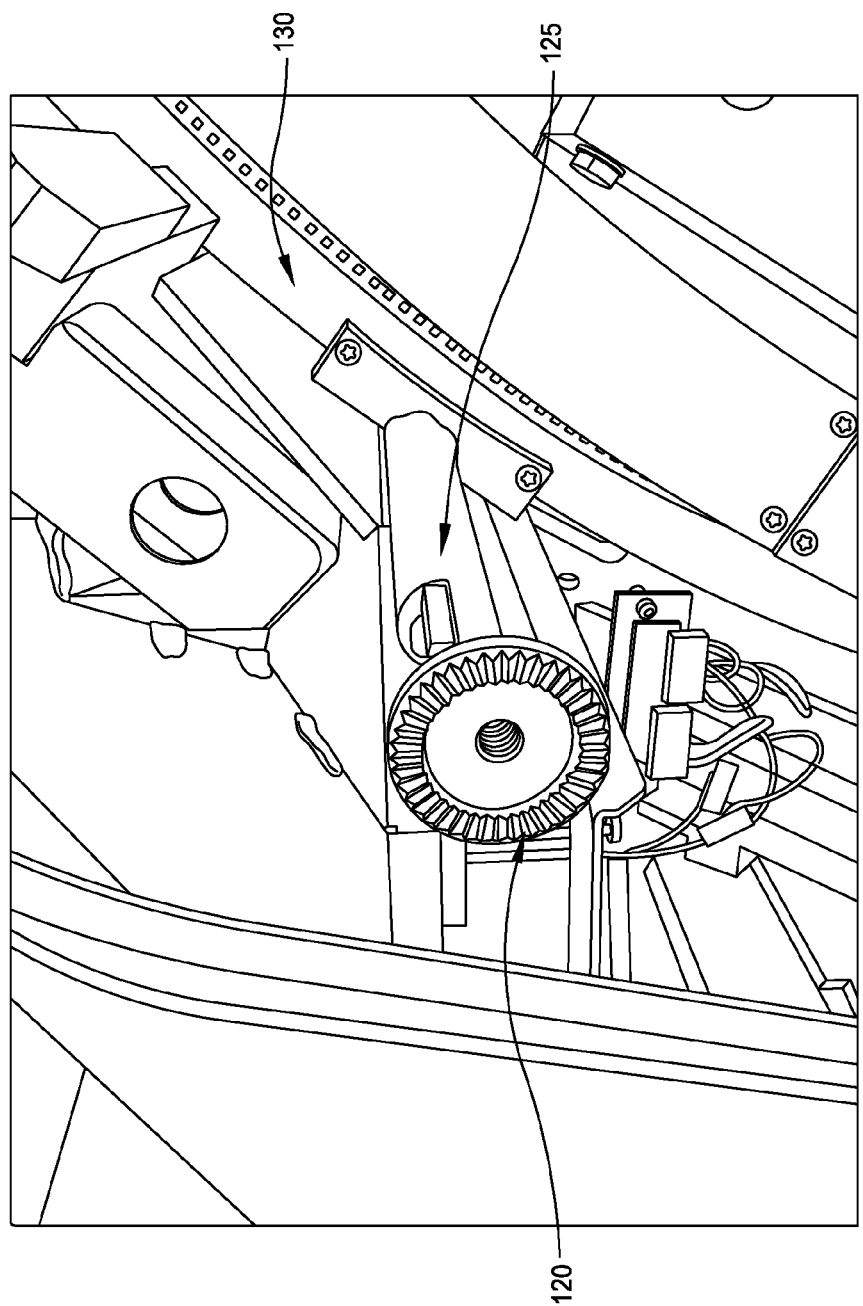
FIG. 13 is a schematic view showing a rigid mount which is rigidly mounted to the scanning components of the imaging system.

In one preferred form of the invention as shown in FIG. 10, the imaging system 100 is a CT imaging system, and the rigid mount 120 is a shaft 125 which is rigidly secured to the gantry 130 of the CT machine. And in one particularly preferred form of the invention, the imaging system of the present invention comprises the CERETOM® mobile CT machine and/or the BODYTOM® mobile CT machine manufactured by NeuroLogica Corporation of Danvers, Mass.

In one preferred form of the invention, the imaging system 100 is connected to the surgical guidance system 102 using a wireless communications system. By way of example but not limitation, imaging system 100 preferably comprises an on-board communications unit 106 and surgical guidance system 102 preferably comprises an on-board communications unit 107, wherein the on-board communications unit 106 of imaging system 100 is configured to wirelessly communicate with the on-board communications unit 107 of surgical guidance system 102, whereby to enable the exchange of data, e.g., images, computer models, etc., therebetween. Preferably the wireless communications system is configured to use a Wireless IEEE 802.11 a/b/g/n transfer protocol, with the connection being configured as either an ad-hoc point-to-point network or as access points through a router. The image transfer syntax is compliant with the DICOM 3.1 standard for medical image transfer or other transfer protocols.

If desired, the rigid mounts 120 of the present invention may also be used to mount other objects to the imaging system 100, e.g., a medical instrument such as a medical laser, a radiotherapy "gun", a robotic arm, a display, a camera, lead curtains, etc.

Non-Medical Applications

In the preceding discussion, the present invention is discussed in the context of medical applications, e.g., scanning anatomy in order to provide a physician with information about that anatomy and/or to provide images to a surgical guidance system whereby to provide surgical guidance to a physician during a surgical procedure. However, it is also possible to use the present invention in non-medical applications, e.g., to scan objects for security purposes (such as luggage, handbags, backpacks, packages, shipping containers, etc. at an airport security station, etc.) and/or to provide images to an operational guidance system whereby to provide operational guidance to a user during an operational procedure (such as remote bomb deactivation, etc.).

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:
1. An imaging system comprising:
   a scanner comprising:
      scanning components for creating an image of an interior portion of an object;
      an outer cover disposed over the scanning components, wherein the outer cover comprises an opening; and
      a rigid mount which is rigidly mounted to the scanning components and extends through the opening in the outer cover.

2. An imaging system according to claim 1, further comprising a fiducial marker mounted to the rigid mount.

3. An imaging system according to claim 1, further comprising a unit mounted to the rigid mount, wherein the unit comprises one from the group consisting of a fiducial marker, a laser, a radiotherapy gun, a robotic arm, a display, a camera, and a lead curtain.

4. An imaging system according to claim 1, wherein the scanner comprises a CT imaging system, wherein the CT imaging system comprises a gantry, and further wherein the rigid mount is rigidly mounted to the gantry of the CT imaging system.

5. An imaging system according to claim 1, wherein the scanning components create an image of an interior portion of organic tissue.

6. An imaging system according to claim 1, wherein the scanning components create an image of an interior portion of at least one from the group consisting of a piece of luggage, a handbag, a backpack, a package, and a shipping container.

7. An imaging system according to claim 1, wherein the scanner comprises at least one from the group consisting of a CT machine, an MRI machine, a PET machine, a SPECT machine, and an ultrasound machine.

8. An imaging system according to claim 1, wherein the scanner is mobile.

9. An imaging system according to claim 8, wherein the scanner moves relative to the object during scanning.

10. An imaging system according to claim 1, wherein the scanner is a fixed-position scanner.

11. An imaging system according to claim 1, further comprising a guidance system for using an image of the interior portion of an object to provide guidance to an individual with respect to the object.

12. An imaging system according to claim 11, wherein the guidance system comprises at least one from the group consisting of a surgical navigation system, a surgical robotics system, a surgical planning system, and another system utilizing image data to provide guidance.

13. An imaging system according to claim 11, wherein the scanner and the guidance system are configured to wirelessly transfer images created by the scanner directly to the guidance system.

14. A method for providing images of an object, the method comprising:
providing a scanner comprising:
scanning components for creating an image of an interior portion of an object;
an outer cover disposed over the scanning components, wherein the outer cover comprises an opening; and
a rigid mount which is rigidly mounted to the scanning components and extends through the opening in the outer cover; and
creating an image of an interior portion of an object using the scanner.

15. A method according to claim 14, further comprising a fiducial marker mounted to the rigid mount.

16. A method according to claim 14, wherein the scanner further comprising a unit mounted to the rigid mount, wherein the unit comprises one from the group consisting of a fiducial marker, a laser, a radiotherapy gun, a robotic arm, a display, a camera, and a lead curtain.

17. A method according to claim 14, wherein the scanner comprises a CT imaging system, wherein the CT imaging system comprises a gantry, and further wherein the rigid mount is rigidly mounted to the gantry of the CT imaging system.

18. A method according to claim 14, wherein the object comprises organic tissue.

19. A method according to claim 14, wherein the object comprises at least one from the group consisting of piece of luggage, a handbag, a backpack, a package, and a shipping container.

20. A method according to claim 14, wherein the scanner comprises at least one from the group consisting of a CT machine, an MRI machine, a PET machine, a SPECT machine, and an ultrasound machine.

21. A method according to claim 14, wherein the scanner is mobile.

22. A method according to claim 21, wherein the scanner moves relative to the object during scanning.

23. A method according to claim 14, wherein the scanner is a fixed-position scanner.

24. A method according to claim 14, further comprising providing a guidance system for using an image of the interior portion of an object to provide guidance to an individual with respect to the object.

25. A method according to claim 24, wherein the guidance system comprises at least one from the group consisting of a surgical navigation system, a surgical robotics system, a surgical planning system, and another system utilizing image data to provide guidance.

26. A method according to claim 24, wherein the scanner and the guidance system are configured to wirelessly transfer images created by the scanner directly to the guidance system.

* * * * *